United States Patent [19]

Masaki

[11] Patent Number: 4,792,702

[45] Date of Patent: Dec. 20, 1988

[54] SWITCH FOR IONTOPHORESING CATION AND ANION

[75] Inventor: Kazumi Masaki, Osaka, Japan

[73] Assignee: Ken Hayashibara, Okayama, Japan

[21] Appl. No.: 105,328

[22] Filed: Oct. 7, 1987

[30] Foreign Application Priority Data

Oct. 11, 1986 [JP] Japan .................. 61-241855

[51] Int. Cl.⁴ .................. H01R 3/06; A61N 1/30; H01H 47/00
[52] U.S. Cl. .................. 307/112; 307/127; 307/141.4; 361/246; 361/245; 128/802; 128/419 R
[58] Field of Search .................. 307/38, 130, 131 R, 307/132 R, 141, 141.4, 138, 139, 112, 127; 200/38 R, 37 R, 37 A, 38 A, 38 F, 38 FA, 38 FB, 38 B, 38 BA, 38 CA, 38 D, 304, 330, 11 G; 361/245, 246; 128/419 R, 639, 798, 803, 802, 795; 604/20

[56] References Cited

U.S. PATENT DOCUMENTS

| 2,622,134 | 12/1952 | Sturges | 361/245 |
| 2,760,143 | 8/1956 | Streuber et al. | 361/246 X |
| 2,964,620 | 12/1960 | Schulenberg | 361/245 X |
| 3,046,421 | 7/1962 | Holzer | 307/141 |
| 3,118,101 | 1/1964 | Arber | 361/246 X |
| 3,140,424 | 7/1964 | Stech | 361/246 |
| 3,162,777 | 12/1964 | Weber et al. | 307/141.4 |
| 3,182,212 | 5/1965 | Weber et al. | 307/141.4 |
| 3,359,392 | 12/1967 | Heath | . |
| 3,365,582 | 1/1968 | Mellinger | 307/141 |
| 4,204,243 | 5/1980 | Ross | 361/245 |
| 4,224,529 | 4/1980 | Fujiwara | 361/246 X |
| 4,323,073 | 4/1982 | Ferris | 128/419 R |
| 4,406,658 | 9/1983 | Lattin et al. | 128/802 X |

FOREIGN PATENT DOCUMENTS

| 0230153 | 7/1987 | European Pat. Off. . |
| 2409524 | 9/1975 | Fed. Rep. of Germany . |
| 3300947 | 5/1985 | Fed. Rep. of Germany . |
| 139672 | 6/1987 | Japan . |
| 159661 | 7/1987 | Japan . |

OTHER PUBLICATIONS

Takanal, Kankoh-So No. 301, "Stimulant for Hair Growth".

Primary Examiner—William M. Shoop, Jr.
Assistant Examiner—Paul Ip
Attorney, Agent, or Firm—Browdy and Neimark

[57] ABSTRACT

Disclosed is a novel switch for iontophoresing cation and anion, comprising an on/off switch for power circuit; a selector switch for reversing the output current from an iontophoretic low-frequency oscillator; and a rotary member actuating said on/off- and selector-switches when turned.

4 Claims, 3 Drawing Sheets

SWITCH FOR IONTOPHORESING CATION AND ANION

BACKGROUND OF THE INVENTION

1. Field of the invention

The present invention relates to a switch for iontophoresing cation and anion.

2. Description of the prior art

Although Kankho-so No. 301 or 6-[2-[(5-bromo-2-pyridyl) amino] vinyl]-1-ethyl-2-picolinium iodide, a photosensitizing dye with an activity of accelerating the growth and regeneration of hair, chemical formula of $C_{15}H_{17}BrN_3{}^+I^-$, molecular weight of 446.14, commercialized by Nippon Kankoh-Shikiso Kenkyusho Co., Ltd., Okayama, Japan, exerts the activity even when applied on the scalp, the activity can be augmented by iontophoresis. The results of my experiments confirm that the activity is extremely augmented by iontophoresing the cation and anion at a duration ratio of 1:2 or 1:3.

SUMMARY OF THE INVENTION

One object of the present invention is to provide a switch means which automatically reverses the output current form an iontophoretic low-frequency oscillator whenever an on/off switch in the power circuit is closed so that cation and anion are iontophoresed at a prescribed ratio.

This and other objects as may become apparent hereinafter have been attained with a switch for iontophoresing cation and anion, characterized in that it comprises an on/off switch for power circuit; a selector switch for selecting the direction of the output current from an iontophoretic low-frequency oscillator; and a rotary member actuating said on/off- and selector-switches when turned.

BRIEF DESCRIPTION OF THE DRAWINGS

Throughout the accompanying drawings, reference numeral (1) designates rotary shaft; (2), knob; (3), cam plate; (4), on/off switch; (5), battery; (6), iontophoretic low-frequency oscillator; (7) and (8), selector switches; (9) and (10), treatment electrodes; (11), rotary disc; (12), rotary shaft; (13), contact terminal of on/off switch; (14) and (15), slidable pieces for operating on/off switch; (16) and (17), contact terminals for operating selector switch; (18), (19), (20) and (21), slidable pieces for operating selector switch; and (22), rotary cylinder.

DESCRIPTION OF THE PREFERRED EMBODIMENTS

The present invention will hereinafter be explained with reference to the drawings.

Figure 1:
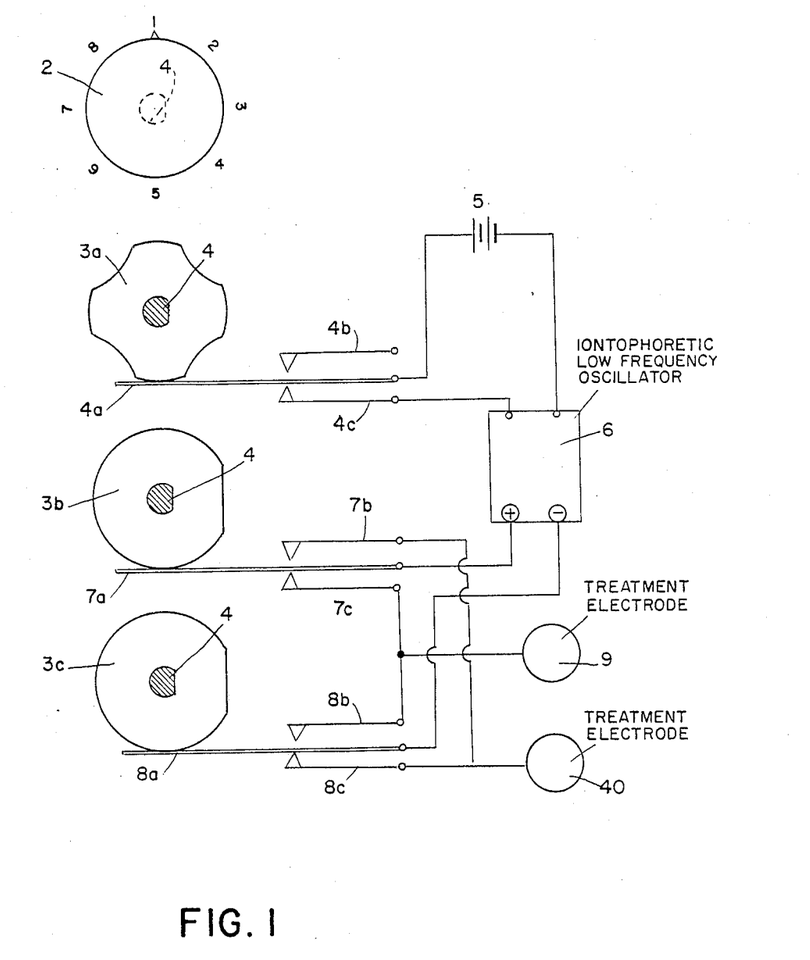
FIG. 1 is the development of an embodiment wherein a plurality of cam plate is provided around a rotary shaft so that an on/off switch and a selection switch are actuated by cam plates.

FIG. 1 is illustrative of an embodiment according to the invention, wherein a plurality of cam plate is provided on a rotary shaft so that an on/off switch for power circuit and a selector switch for reversing the output current from an iontophorectic low-frequency oscillator can be actuated by turning the cam plates. Reference numeral (1) designates the rotary shaft actuated by knob (2). Reference numerals (3a), (3b) and (3c) designate the cam plates supported by rotary shaft (1), and the cam plates can be turned by moving rotary shaft (1) with knob (2). Reference numeral (4) designates the on/off switch actuated by moving movable piece (4a) with cam plate (3a), and the on/off switch closes and opens the power circuit when they come into contact respectively with fixed pieces (4b) and (4c). Reference numeral (5) designates the battery as the power source. Reference numeral (6) designates the iontophoretic low-frequency oscillator comprising, for example, a blocking oscillator or a multivibrator. Reference numeral (7) designates a selector switch for selecting "plus" output current from iontophoretic low-frequency oscillator (6). Switch (7) opens and closes the circuit when actuated by moving movable piece (7a) with cam plate (3b) to contact movable piece (7a) with fixed pieces (7b) and (7c). Reference numeral (8) designates a selector switch for selecting "minus" output current from iontophoretic low-frequency oscillator (6). Switch (8) opens and closes the circuit when actuated by moving movable piece (8a) with cam plate (3c) to contact movable piece (8a) respectively with fixed pieces (8b) and (8c).

Now supposing that knob (2) is at position "1" as shown in FIG. 1, movable piece (4a) for operating on/off switch (4) is pushed downwardly by cam plate (3a) and allowed to come into contact with fixed piece (4c) to turn the power circuit on. Thus, battery (5) powers low-frequency oscillator (6).

At this time, cam plates (3b) and (3c) depress movable pieces (7a) and (7b) to contact respectively with fixed piece (7c) and (8c). With this, a positive potential from low-frequency oscillator (6) energizes treatment electrode (9) through movable piece (7a) and fixed piece (7c), while a negative potential from low-frequency oscillator (6) energizes treatment electrode (10) through movable piece (8a) and fixed piece (8c) of selector switch (8). Thus, by placing treatment electrodes (9) and (10) on the subject's skin, cation and anion are iontophoresed respectively by treatment electrodes (9) and (10).

When knob (2) is turned to position "2", spring-supported movable piece (4a) of on/off switch (4) is pushed upwardly by the indented part of cam plate (3a) and allowed to contact with fixed piece (4b) to turn the power circuit off. Thus, battery (5) stops powering low-frequency oscillator (6).

When knob (2) is turned to position "3", movable piece (4a) of power switch (4) is depressed by the projection of cam plate (3a) and allowed to come into contact with fixed piece (4c) to turn the power circuit on. Thus, battery (5) powers low-frequency oscillator (6).

Since with this the cutaways of cam plates (3b) and (3c) come into contact respectively with movable pieces (7a) and (8a) of selector switches (7) and (8), movable pieces (7a) and (8a) are pushed upwardly by a spring and comes into contact with fixed pieces (7b) and (8b). Thus, a positive potential from low-frequency oscillator (6) energizes treatment electrode (9) through movable piece (7a) and fixed piece (7b) of selector switch (7), while a negative potential energizes treatment electrode (10) through movable piece (8a) and fixed piece (8b) of selector switch (8). Inversely at position "1" anion and cation are iontophoresed respectively by treatment electrodes (9) and (10).

Since the power circuit opens when knob (2) comes to position "4", the operation of low-frequency oscillator (6) is suspended. At position "5", the power circuit closes, and treatment electrodes (9) and (10) are energized respectively with positive and negative potentials from low-frequency oscillator (6) as in the case at position "1".

Since the power circuit reopens when knob (2) is turned to position "6", the operation of low-frequency oscillator (6) is suspended. When knob (2) is turned to position "7", the power circuit closes and treatment electrodes (9) and (10) are energized respectively with positive and negative potentials as in the case at position "1" or "5".

The power circuit closes when knob (2) is turned to position "8" to suspend the operation of low-frequency oscillator (6). In this way, one selection cycle is completed.

The voltage across treatment electrode (9) becomes successively "plus", "minus", "plus" and "plus" in one selection cycle, while that across treatment electrode (10) becomes successively "minus", "plus", "minus" and "minus" whenever an off/on operation of switch (4) is effected by turning knob (2).

By applying a medicament on treatment electrode (10) and turning knob (2), iontophoresis of anion is effected three times per cycle, while that of cation is effected one time per cycle. Attachment of a backlash eliminating means, such as gear with a free wheel pawl, to knob (2) is desirable.

Figure 2:
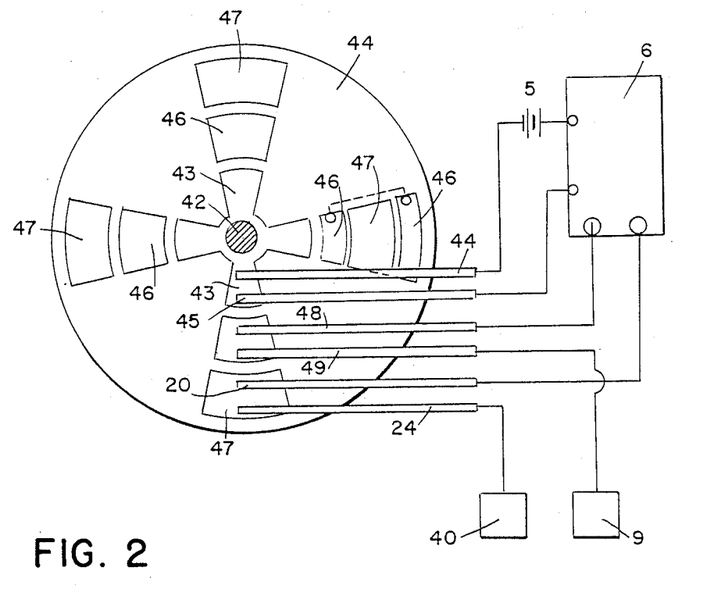
FIG. 2 is the development of another embodiment wherein a plurality of contact terminal radially provided on a rotary disc is used to actuate on/off- and selector-switches.

FIG. 2 is illustrative of another embodiment according to the invention, wherein a plurality of contact terminal provided radially on a rotary disc is used to actuate an on/off switch for power circuit and a selector switch for reversing the output current from a low-frequency oscillator. Reference numeral (11) designates the rotary disc rotatably provided around rotary shaft (12). Reference numeral (13) designates a contact terminal of the on/off switch for a power circuit including battery (5), and the contact terminal contacts elastically with rotary disc (11) so that slidable pieces (14) and (15) in the on/off switch can contact each other. Reference numeral (16) designates a contact terminal of the selector switch for selecting "plus" output current from iontophoretic low-frequency oscillator (6), while reference numeral (17) designates a contact terminal of the selector switch for selecting "minus" output current. Contact terminals (16) and (17) and slidable pieces (18), (19), (20) and (21) can contact elastically with rotary disc (11), and the slidable pieces are parts of the selector switch. Contact terminals (16) and (17) and slidable pieces (18), (19), (20) and (21) must be arranged in such manner that contact terminal (16) can contact with slidable pieces (18) and (19), and that contact terminal (17) can contact with slidable pieces (20) and (21) when contact terminal (13) is in contact with slidable pieces (14) and (15). Thus, contact terminals (13), (16) and (17) must be arranged linerly with respect to the radius of rotary disc (11). Contact terminals (13), (16) and (17) are provided on rotary disc (11) usually in plurality; in the embodiment as shown in FIG. 2, four sets of the contact terminals are provided. The shape of one contact terminal set is slightly modified in order to change the contact conditions with slidable pieces (18), (19), (20) and (21).

When as shown in FIG. 2 slidable pieces (14) and (15) are in contact with contact terminal (13) of the on/off switch, the power circuit is on and low-frequency oscillator (6) is powered by battery (5). Since at this time slidable pieces (18) and (19) are also in contact with contact terminal (16) of the selector switch for selecting "plus" output current, a positive potential from low-frequency oscillator (6) energizes treatment electrode (9) through slidable piece (18), contact terminal (16) of the selector switch and slidable piece (19). Since slidable pieces (20) and (21) are in contact with contact terminal (17) of the selector switch for selecting "minus" output current, a negative potential from low-frequency oscillator (6) energizes treatment electrode (10) through slidable piece (20), contact terminal (17) of selection switch, and slidable piece (21).

By turning rotary disc (11) to open the contact between slidable piece (14) and (15) and contact terminal (13), the power circuit is turned off and the operation of low-frequency oscillator (6) is suspended.

By further turning rotary disc (11) to contact slidable pieces (14) and (15) with contact terminal (13), the power circuit closes and battery (5) powers low-frequency oscillator (6). Since at this time slidable pieces (18) and (21) are in contact with modified contact terminal (16) of the selector switch for selecting "plus" output current, a positive potential from low-frequency oscillator (6) energizes treatment electrode (10), while a negative potential energizes treatment electrode (9) because slidable pieces (19) and (20) are in contact with modified contact terminal (17) of the selector switch for selecting "minus" output current.

In this way, during one selection cycle of rotary disc (11), a positive potential and a negative potential energize treatment electrodes (9) and (10) at a selection ratio of 1:3. In other words, iontophoresis of cation is effected one time per cycle, while that of anion is effected three times per cycle.

Figure 3:
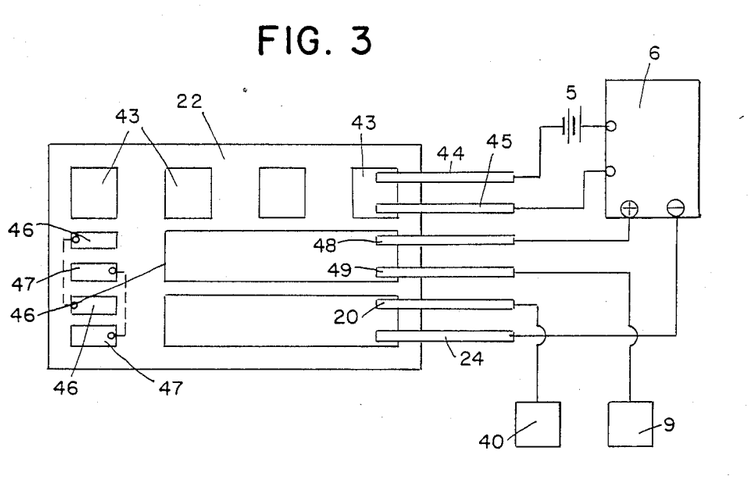
FIG. 3 is the development of still another embodiment according to the invention wherein plurality of contact terminal provided on the circumferential of a rotary cylinder is used to actuate on/off- and selector-switches.

FIG. 3 is illustrative of still another embodiment according to the invention, wherein a plurality of contact terminal is provided on the circumferential surface of a rotary cylinder to leave appropriate intervals therebetween so that the contact terminals can actuate an on/off switch for power circuit and a selector switch for reversing the output current from a low-frequency oscillator. Reference numeral (22) designates the rotary cylinder rotatably provided around rotary axis. FIG. 3 illustrates the development of rotary cylinder (22). Rotary cylinder (22) is replaced for rotary disc (11) as used in FIG. 2, and on the circumferential surface contact terminal (13) for on/off switch, and contact terminals (16) and (17) for the selector switch are provided at appropriate intervals. Slidable pieces (14), (15), (18), (19), (20) and (21) can elastically contact with the circumferential surface of rotary cylinder (22) so that the slidable pieces provide on/off- and selector-switches with contact terminals (13), (16) and (17). Since the selector switch can be actuated by turning rotary cylinder similarly as rotary disc (11) as in FIG. 2, iontophoresis of cation and anion can be appropriately controlled.

Figure 4:
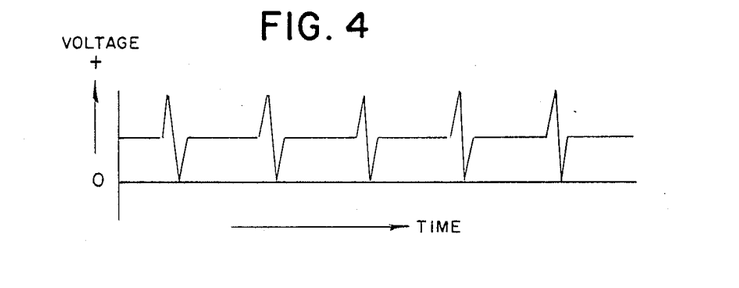
FIGS. 4 and 5 are the output waveforms of a low-frequency oscillator.
Figure 5:
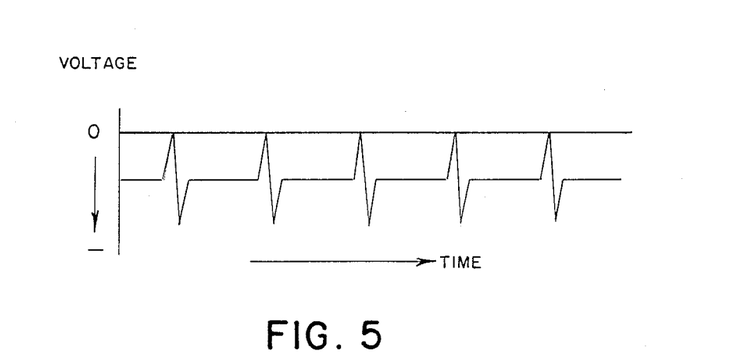

FIGS. 4 and 5 are illustrative of the output waveforms of low-frequency oscillator (6). FIG. 4 is illustrative of the waveform of the positive output potential for iontophoresing cations; and FIG. 5, the waveform of the negative output potential for iontophoresing anions.

The present invention is characterized in that medicaments such as hair restorer can be efficiently iontophoresed because iontophoresis of cation and anion can be controlled to a prescribed selection ratio.

While preferred embodiments have been described, variations thereto will occur to those skilled in the art within the scope of the present invention concepts which are delineated by the following claims.

I claim:

1. A switch directed to use in a low-frequency oscillator to iontophorese 6-[2-[(5-bromo-2-pyridyl) amino] vinyl]-1-ethyl-2-picolinium iodide into the scalp, comprising:
    an on/off switch to control a power circuit of an iontophoretic low-frequency oscillator;
    a selector switch to reverse an output current from said iontophoretic low-frequency oscillator in such manner that a positive potential and a negative potential energize an electrode containing 6-[2-[(5-bromo-2-pyridyl) amino] vinyl]-1-ethyl-2-picolinium iodine at a duration ratio of 1:2 or 1:3 during one selection cycle; and
    a rotary member actuating said on/off- and selector-switches when turned.

2. The switch of claim 1, wherein said rotary member comprises a plurality of cam plate provided on a rotary shaft, said cam plates actuating sain on/off- and selector-switches when turned.

3. The switch of claim 1, wherein said rotary member comprises a rotary disc including a plurality of contact terminal radially provided on the surface of said rotary disc, said rotary disc actuating slidable pieces of said on/off- and selector-switches when turned, said slidable pieces being provided in contact with said rotary disc.

4. The switch of claim 1, wherein said rotary member comprises a rotary cylinder including a plurality of contact terminal provided on the circumferential surface of said rotary cylinder, said rotary cylinder actuating slidable pieces of said on/off- and selector-switches when turned, said slidable pieces being provided in contact with the circumferential surface of said rotary cylinder.

* * * * *

UNITED STATES PATENT AND TRADEMARK OFFICE
CERTIFICATE OF CORRECTION

PATENT NO. : 4,792,702

DATED : December 20, 1988

INVENTOR(S) : Kazumi Masaki

It is certified that error appears in the above-identified patent and that said Letters Patent is hereby corrected as shown below:

The title page should be deleted to appear as per attached page.

The sheets of Drawings consisting of Figs. 1-3, should be deleted to appear as per attached pages.

Signed and Sealed this

Twenty-second Day of September, 1992

*Attest:*

DOUGLAS B. COMER

*Attesting Officer*   *Acting Commissioner of Patents and Trademarks*

United States Patent [19]

Masaki

[11] Patent Number: 4,792,702
[45] Date of Patent: Dec. 20, 1988

[54] SWITCH FOR IONTOPHORESING CATION AND ANION

[75] Inventor: Kazumi Masaki, Osaka, Japan

[73] Assignee: Ken Hayashibara, Okayama, Japan

[21] Appl. No.: 105,328

[22] Filed: Oct. 7, 1987

[30] Foreign Application Priority Data

Oct. 11, 1986 [JP] Japan .................. 61-241855

[51] Int. Cl.[4] .................. H01R 3/06; A61N 1/30; H01H 47/00
[52] U.S. Cl. .................. 307/112; 307/127; 307/141.4; 361/246; 361/245; 128/802; 128/419 R
[58] Field of Search .......... 307/38, 130, 131 R, 307/132 R, 141, 141.4, 138, 139, 112, 127; 200/38 R, 37 R, 37 A, 38 A, 38 F, 38 FA, 38 FB, 38 B, 38 BA, 38 CA, 38 D, 304, 330, 11 G; 361/245, 246; 128/419 R, 639, 798, 803, 802, 795; 604/20

[56] References Cited

U.S. PATENT DOCUMENTS

| | | | |
|---|---|---|---|
| 2,622,134 | 12/1952 | Sturges | 361/245 |
| 2,760,143 | 8/1956 | Streuber et al. | 361/246 X |
| 2,964,620 | 12/1960 | Schulenberg | 361/245 X |
| 3,046,421 | 7/1962 | Holzer | 307/141 |
| 3,118,101 | 1/1964 | Arber | 361/246 X |
| 3,140,424 | 7/1964 | ech | 361/246 |
| 3,162,777 | 12/1964 | Weber et al. | 307/141.4 |
| 3,182,212 | 5/1965 | Weber et al. | 307/141.4 |
| 3,359,392 | 12/1967 | Heath | |
| 3,365,582 | 1/1968 | Mellinger | 307/141 |
| 4,204,243 | 5/1980 | Ross | 361/245 |
| 4,224,529 | 4/1980 | Fujiwara | 361/246 X |
| 4,323,073 | 4/1982 | Ferris | 128/419 R |
| 4,406,658 | 9/1983 | Lattin et al. | 128/802 X |

FOREIGN PATENT DOCUMENTS

| | | |
|---|---|---|
| 0230153 | 7/1987 | European Pat. Off. |
| 2409524 | 9/1975 | Fed. Rep. of Germany |
| 3300947 | 5/1985 | Fed. Rep. of Germany |
| 139672 | 6/1987 | Japan |
| 159661 | 7/1987 | Japan |

OTHER PUBLICATIONS

Takanal, Kankoh-So No. 301, "Stimulant for Hair Growth".

Primary Examiner—William M. Shoop, Jr.
Assistant Examiner—Paul Ip
Attorney, Agent, or Firm—Browdy and Neimark

[57] ABSTRACT

Disclosed is a novel switch for iontophoresing cation and anion, comprising an on/off switch for power circuit; a selector switch for reversing the output current from an iontophoretic low-frequency oscillator; and a rotary member actuating said on/off- and selector-switches when turned.

4 Claims, 3 Drawing Sheets

UNITED STATES PATENT AND TRADEMARK OFFICE
CERTIFICATE OF CORRECTION

Page 3 of 5

PATENT NO. : 4,792,702
DATED : December 20, 1988
INVENTOR(S) : Kazumi MASAKI

It is certified that error appears in the above-identified patent and that said Letters Patent is hereby corrected as shown below:

FIG. I

UNITED STATES PATENT AND TRADEMARK OFFICE
CERTIFICATE OF CORRECTION

PATENT NO. : 4,792,702
DATED : December 20, 1988
INVENTOR(S) : Kazumi MASAKI

It is certified that error appears in the above-identified patent and that said Letters Patent is hereby corrected as shown below:

FIG. 2

UNITED STATES PATENT AND TRADEMARK OFFICE
CERTIFICATE OF CORRECTION

PATENT NO. : 4,792,702

DATED : December 20, 1988

INVENTOR(S) : Kazumi MASAKI

It is certified that error appears in the above-identified patent and that said Letters Patent is hereby corrected as shown below:

FIG. 3